United States Patent [19]

Stewart et al.

[11] 4,076,950

[45] Feb. 28, 1978

[54] PROCESS FOR MANUFACTURE OF ALKYL ESTERS OF ALIPHATIC CARBOXYLIC ACIDS

[75] Inventors: Thomas Stewart, Andalusia; Frederick W. Landau, Havertown, both of Pa.

[73] Assignee: Rohm and Haas Company, Philadelphia, Pa.

[21] Appl. No.: 706,646

[22] Filed: Jul. 19, 1976

[51] Int. Cl.$^2$ ............................................. C07C 69/54
[52] U.S. Cl. .................................... 560/218; 203/60
[58] Field of Search ...................... 260/486 R; 203/60

[56] References Cited

U.S. PATENT DOCUMENTS 3,354,199  11/1967  Lachowicz et al. .................. 203/60
3,527,677   9/1970  Harpring ..................... 203/DIG. 21
3,553,261   1/1971  Sennewald et al. .................. 203/60
3,666,632   5/1972  Honda et al. ......................... 203/60

Primary Examiner—Paul J. Killos
Attorney, Agent, or Firm—George W. F. Simmons; Jordan J. Driks

[57] ABSTRACT

A continuous process for the preparation of acrylic and methacrylic acid esters by conventional esterification, where sufficient substantially anhydrous product ester is added to the esterification reactor to satisfy the ester-/alkanol and ester/water azeotropes, the low boiling azeotropes are recovered, thereby removing crude product ester, unreacted alkanol and water of esterification from the esterification reactor, while leaving substantially all the high-boiling unreacted acrylic or methacrylic acid in the reactor.

5 Claims, 1 Drawing Figure

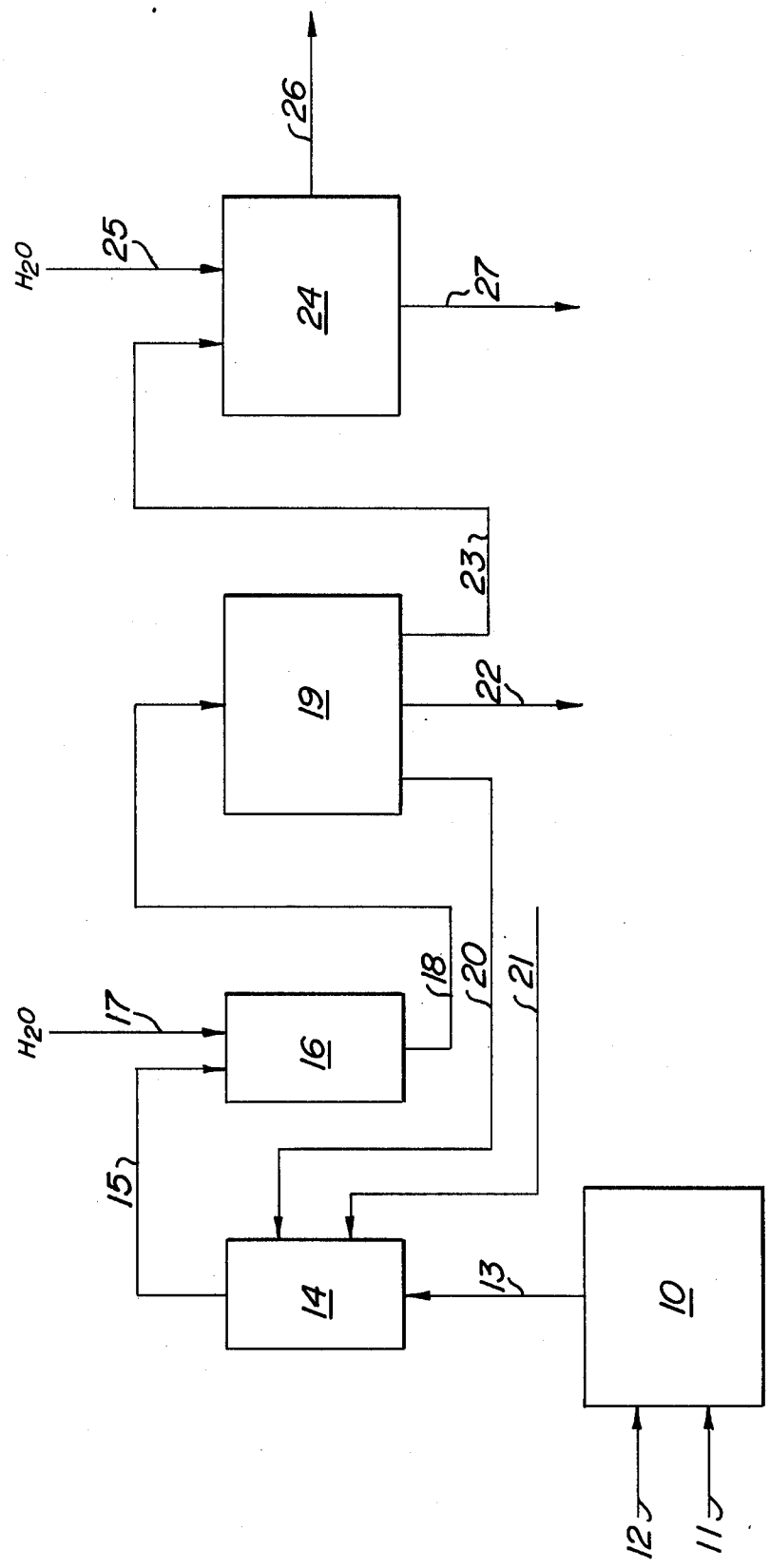

PROCESS FOR MANUFACTURE OF ALKYL ESTERS OF ALIPHATIC CARBOXYLIC ACIDS

This invention relates to an improved process for continuously preparing acrylic and methacrylic acid esters and recovering them as crude product esters substantially free of unreacted (meth)acrylic acid.

In the preparation of acrylic and methacrylic acid esters, as by acid-catalyzed esterification of the acids with alkanols, the normal product recovery procedure involves distilling the reaction mixture so at to take overhead as distillate a mixture of crude ester, water of esterification and unreacted alkanol and (meth)acrylic acid. After aqueous and organic phase separation, the organic phase is treated with an alkaline material, such as ammonia, so as to neutralize the phase and thereby remove the unreacted (meth)acrylic acid. The neutralized organic phase is then washed with water in a further separator to remove unreacted alkanol and finally treated in a dehydration column so as to dry the ester.

However, this procedure is often beset with several problems characteristic of such recovery procedures. The primary problem is the presence of the (meth)acrylic acid salt produced during neutralization, such as for example ammonium (meth)acrylate, in the processing steps between the distillation column and dehydration column. The most significant problem is that the salt leads to formation of polymer in the dehydration column. After neutralization of the organic phase, an emulsion in the form of an aqueous phase of (meth)acrylate salt occluded in the organic phase often occurs during the subsequent phase separation. This emulsion is often not separable even after long standing. Further addition of alkaline material to break the emulsion can be erratic and, often, excess material is added. When this emulsion is fed to the dehydration column, the dissolved salts often lead to polymer formation.

These problems are most acute with methyl acrylate. This ester has a density closest to that of water. When methanol is present in the organic and aqueous phases, the difference in density becomes even less, with increased problems in ester/water gravity separators. If, for example, excess ammonia is present in the neutralization, the density of the ammonium acrylate phase is lowered, making the neutralization separation even more difficult, thus assuring presence of ammonium acrylate in the crude ester phase.

These problems can be avoided by obtaining a crude ester distillate that is substantially free of unreacted carboxylic acid, so that only a "polish" neutralization is required, where even if emulsion does form, it can be readily broken by sufficient water-washing in a further separator. But if the (meth)acrylic acid is fractionated so that it remains in the reactor, then water of esterification is not removed from the reactor. The presence of water of esterification has a detrimental effect on the esterification reaction equilibrium and, thus, must be removed. The present invention, however, has simultaneously solved the problems of obtaining a crude ester distillate substantially free of unreacted carboxylic acid and of removing water of esterification from the esterification reactor.

Thus, in a process for the preparation of acrylic and methacrylic acid esters by conventional esterification processes, wherein crude product ester is recovered as distillate from an esterification reactor together with unreacted alkanol, unreacted carboxylic acid and water of esterification by fractional distillation, the improvement is that of obtaining a crude ester distillate substantially free of unreacted carboxylic acid by adding to the reactor sufficient substantially anhydrous product ester, thereby satisfying combined ester/alkanol and ester/water azeotropes so that unreacted carboxylic acid remains in the reactor and the combined azeotropes are distilled over as crude product.

The common problem involved in crude ester recovery, as for example in recovery of methyl acrylate, is the fact that unreacted acrylic acid distills from the reactor in the water of esterification. Thus, under unmodified recovery conditions, distillation of crude product ester from the reactor involves taking unreacted carboxylic acid overhead in the water of esterification. If an acid-free distillate is desired, the water of esterification must be selectively removed while leaving unreacted acid in the reactor. Thus, if the water could be azeotropically removed, little or no unreacted carboxylic acid would be taken overhead.

This situation can be achieved by returning or adding to the reactor of sufficient quantity of substantially anhydrous product ester, low in unreacted alkanol, so as to satisfy the ester/water and ester/alkanol azeotropes. The azeotropes, having boiling points substantially lower than the unreacted carboxylic acid, are alone taken overhead. Since the carboxylic acids do not azeotrope, it becomes possible to remove crude product ester and water of esterification while leaving the unreacted carboxylic acid in the reactor.

The substantially anhydrous crude product ester of low alkanol content to be used for adding back to the reactor can be obtained from several sources. It has been found that if the crude product ester distillate from the reactor is water-washed in the ester condenser, the organic/aqueous phase separation is greatly enhanced. Thus, for example, in the preparation of methyl acrylate, if the crude distillate (i.e., vapor of organic and aqueous material from the ester reactor column) is contacted with a stream of water in the distillate condenser, the improved phase separation achieved provides an organic phase rich in methyl acrylate ($\geq 95\%$) and low in menthanol ($\leq 2\%$) and water ($\leq 3\%$). This substantially anhydrous crude product ester can then be returned to the ester reactor, as by refluxing, so as to satisfy the methyl acrylate/methanol and methyl acrylate/water azeotropes. However, it is also possible to augment this washed crude product ester with product ester obtained after "polish" neutralization or product ester obtained from the dehydration column. Likewise, the latter sources of product ester could be added to the ester reactor to the exclusion of the condenser water-washed crude ester refluxed from the gravity separator.

The acids that can be esterified by the improved process include acrylic acid and α-alkyl acrylic acids, such as methacrylic acid. The alcohols used are generally the lower alkanols, such as for example methanol, ethanol, the propanols, the butanols and the like.

The ester preparation can be by the known process of contacting acid and alcohol in the presence of an acid catalyst. The preferred catalysts are those that are thermally stable and of low volatility. Examples include sulfuric acid, phosphoric acid, benzenesulfonic acid and toluenesulfonic acid. Acid anhydrides may also be used, such as for example phosphoric pentoxide and sulfur trioxide. The acid catalysts may also be absorbed onto solid supports, such as for example magnesia, silica, alumina, keiselguhr, and the like, so that the carboxylic acid and alcohol can pass freely through a bed of the catalyst. Polymerization inhibitors, for example, hydroquinone, can be added to the carboxylic acid solution prior to vaporization.

The reaction parameters are, of course, dictated by the nature of the ester being prepared. In general, however, reaction temperatures of about 50° C to 150° C can be employed, and pressures can vary from approximately 200 mm to atomspheric. It is preferable that the alcohol be in a slight excess relative to the acid. Thus, ratios can, for example, be in the alcohol to carboxylic acid range of about 1–1.6:1, preferably in the range 1.05–1.5:1, and more preferably 1.1–1.35:1.

The present invention will be more readily apparent by reference to the drawing.

The FIGURE is a schematic flow diagram showing one embodiment of the present invention, the invention being not limited thereto.

Meth(acrylic) acid and alcohol are fed to the esterification reactor 10 through line 11, and the acid catalyst thereto through line 12. The reactants may all be fed separately to the reactor. The unreacted reactants, water of esterification and product ester are then sent via line 13 to fractionation column 14. Substantially anhydrous product ester is fed to the fractionation column 14 by lines 20 and 21. By the preferred embodiment, reflux of substantially anhydrous product ester from the first phase separator 19 is refluxed to the column 14. However, the reflux may be supplemented by substantially anhydrous ester from other sources, or the reflux may be completely replaced by this alternate source, in either case the alternate ester being provided to the column 14 through line 21.

The combination of product ester from the reactor 10 and the additional ester obtained by lines 20 and/or 21 satisfies the ester/water and ester/alcohol azeotropes, whereby water of esterification, product ester and unreacted alcohol are taken overhead via line 15 and fed to the condenser 16, the unreacted carboxylic acid remaining in the reactor 10. The vapors taken overhead via line 15 are washed in condenser 16 with water fed thereto via line 17. The washed overhead is then fed via line 18 to the first phase separator 19. The condenser water wash allows substantially anhydrous product ester to be separated from the aqueous phase of the overhead, and part of this, preferably, is refluxed via line 20 to the fractionation column 14. The aqueous phase from separator 19 may be collected via line 22. It is preferable that the separated ester not returned to the column 14 be given a second wash and separation. Thus, ester to be recovered is fed via line 23 to the second phase separator 24, where the ester is washed with water fed thereto through line 25. After separation, the ester is fed to a dehydration column via line 26, while the aqueous phase is either processed for recovery of recyclable organics or flushed to waste via line 27.

The following examples will further elucidate the present invention.

EXAMPLE 1

Methyl acrylate is prepared by reacting acrylic acid and methanol in the presence of sulfuric acid as catalyst in a 3-liter flask (liquid volume being maintained at 2400 mls). A 15 plate, 2" Oldershaw distillation column is fitted to the flask. To the Oldershaw distillation column are attached two condensers, both of which connect to a 300 ml water-jacketed horizontal separator with metering stopcock. Steady state reaction parameters are given in Table I. The crude distillate is taken overhead, washed in the condenser, separated, and the water and methanol-depleted organic phase divided so as to give a reflux ratio of 20% forward, the remainder being refluxed back to the Oldershaw column. The results are tabulated in Table II. This table clearly demonstrates that the improved process leaves all the unreacted acrylic acid in the reactor, while removing all of the water of esterification. The yield of methyl acrylate on acrylic acid and methanol is extremely high.

EXAMPLE 2

In this example, the esterification of Example 1 is carried out without return of sufficient methyl acrylate to the ester reactor and with no addition of water to the condenser. The reflux feed is typical of a stream from the methyl acrylate purification scheme. The reaction parameters are given in Table III and the results in Table IV. As can be seen, the concentration of water in the reactor varies between 25–35%, while the organic phase of the distillate contains about 0.2–0.9% acrylic acid. The water in the reactor builds up until it distills out of the reactor, carrying acrylic acid with it. This acrylic acid must then be neutralized and removed from the product ester.

TABLE I

| Reflux Ratio | Pot Temp. °C | Vapor Temp. °C | Press. (mms) | Feed/hr Moles MeOH | Feed/hr Moles AA | Feed/hr (g) $H_2SO_4$ | Water (g) to Condenser |
| --- | --- | --- | --- | --- | --- | --- | --- |
| 20% Fwd. | 69–74 | 38 | 200 | 5.98 | 5.22 | 12 | 303 |

| Distillate/hr (g) Organic | Distillate/hr (g) Aqueous | Reactor Bleed/hr (g) | Separator Residence Time/Quality |
| --- | --- | --- | --- |
| 379 | 460 | 68 | 16 mins/very good |

TABLE II

| | Organic Distillate/hr | | | | Aqueous Distillate/hr | | | | Reactor Bleed | | | | $H_2SO_4$+High Boilers |
| --- | --- | --- | --- | --- | --- | --- | --- | --- | --- | --- | --- | --- | --- |
| | MA | MeOH | $H_2O$ | AA | MA | MeOH | $H_2O$ | AA | MA | MeOH | $H_2O$ | AA | |
| % | 96.6 | 0.9 | 2.6 | 0 | 5.9 | 6.1 | 88.2 | 0 | 10.0 | 1.4 | 12.5 | 45.0[1] | 31.1 |
| Moles | 4.26 | 0.11 | | | 0.32 | 0.89 | | | 0.08 | 0.03 | | 0.43 | |

Yield of MA on AA $= \dfrac{4.26 + 0.32 + 0.08}{5.22 - 0.43}$ on MeOH $= \dfrac{4.26 + 0.32 + 0.08}{5.98 - 0.11 - 0.89 - 0.03}$

TABLE II-continued

| Organic Distillate/hr | | | | Aqueous Distillate/hr | | | | Reactor Bleed | | | | H$_2$SO$_4$+High |
|---|---|---|---|---|---|---|---|---|---|---|---|---|
| MA | MeOH | H$_2$O | AA | MA | MeOH | H$_2$O | AA | MA | MeOH | H$_2$O | AA | Boilers |
| = $\frac{4.66}{4.79}$ = 97.3% | | | | = $\frac{4.66}{4.95}$ = 94.1% | | | | | | | | Yields are based on converted starting materials. |

[1] As recoverable AA or acryloxypropionic acid.

TABLE III

| Reflux Ratio | Reflux Feed (g/hr) | Pot Temp. °C | Vapor Temp. °C | Press. (mms) | Feed/hr Moles MeOH | Feed/hr Moles AA | Feed/hr (g) H$_2$SO$_4$ |
|---|---|---|---|---|---|---|---|
| 100% Fwd. | 482[1] | 62-75 | 37-49 | 200 | 7.45 | 6.45 | 14.8 |

| Distillate/hr (g) Organic | Distillate/hr (g) Aqueous | Reactor Bleed/hr (g) |
|---|---|---|
| 1013 | 53.5 | 82.3 |

| | % | Moles/hr |
|---|---|---|
| [1]MA | 97.5 | 5.46 |
| MEOH | 0.5 | 0.08 |
| H$_2$O | 2.0 | 0.54 |

TABLE IV

| | Organic Distillate/hr | | | | Aqueous Distillate/hr | | | | Reactor Bleed | | | | H$_2$SO$_4$+High |
|---|---|---|---|---|---|---|---|---|---|---|---|---|---|
| | MA | MeOH | H$_2$O | AA | MA | MeOH | H$_2$O | AA | MA | MeOH | H$_2$O | AA | Boilers |
| % | 92.5 | 3.3 | 4.4 | 0.2– | 6.8 | 14.0 | 78.7 | 0.1– | 9.3 | 1.2 | 28.0 | 14.6 | 46.9 |
| Moles | 10.9 | 1.05 | 2.38 | 0.9 | 0.04 | 0.22 | 2.34 | 0.8 | 0.09 | 0.03 | 1.30 | 0.18 | |

We claim:

1. In a process for the preparation of acrylic and methacrylic acid esters by conventional esterification, wherein crude product ester is recovered as distillate from an esterification reactor together with unreacted alkanol, unreacted carboxylic acid and water of esterification by fractional distillation, the improvement of obtaining a crude ester distillate substantially free of unreacted carboxylic acid by adding to the reactor sufficient substantially anhydrous product ester, thereby satisfying combined ester/alkanol and ester/water azeotropes so that substantially all of the unreacted carboxylic acid remains in the reactor and the combined azeotropes are distilled over as crude product.

2. The process of claim 1, where the substantially crude product ester added to the reactor is by refluxing a part of the crude ester distilled from the reactor.

3. The process of claim 2, where part of the crude ester distilled from the reactor is water-washed prior to being refluxed to the reactor.

4. The process of claim 1, where the ester is methyl acrylate or ethyl acrylate.

5. The process of claim 1, where the ester is selected from the group consisting of methyl acrylate, ethyl acrylate, methyl methacrylate and ethyl methacrylate.

* * * * *